United States Patent [19]

Bender

[11] 4,366,098

[45] Dec. 28, 1982

[54] PROCESS FOR PREPARING AMINOPENICILLINS

[75] Inventor: Reinhold H. W. Bender, Kennett Square, Pa.

[73] Assignee: American Home Products Corporation, New York, N.Y.

[21] Appl. No.: 298,039

[22] Filed: Aug. 31, 1981

Related U.S. Application Data

[63] Continuation-in-part of Ser. No. 210,495, Nov. 26, 1980, abandoned, which is a continuation of Ser. No. 67,632, Aug. 17, 1979, abandoned.

[51] Int. Cl.$^3$ .................. C07D 499/12; C07C 102/04; C07C 103/375
[52] U.S. Cl. ......................... 260/239.1; 260/465 D; 260/501.11; 564/200

[58] Field of Search ..................... 260/239.1

[56] References Cited

U.S. PATENT DOCUMENTS

| | | | |
|---|---|---|---|
| 3,316,247 | 4/1967 | Fosker et al. | 260/239.1 |
| 3,325,479 | 6/1967 | Fosker et al. | 260/239.1 |
| 3,971,775 | 7/1976 | Cowley et al. | 260/239.1 |
| 4,128,547 | 12/1978 | van der Drift et al. | 260/239.1 |

*Primary Examiner*—Natalie Trousof
*Assistant Examiner*—Vera C. Clarke
*Attorney, Agent, or Firm*—George Tarnowski

[57] ABSTRACT

An improved process for the preparation of α-aminopenicillins from an aqueous solution of a derivative of 6-APA and amide-type Dane salts.

7 Claims, No Drawings

PROCESS FOR PREPARING AMINOPENICILLINS

This is a continuation-in-part of Ser. No. 210,495 filed Nov. 26, 1980, now abandoned, which is a continuation of Ser. No. 067,632 filed Aug. 17, 1979, now abandoned.

BACKGROUND OF THE INVENTION

The α-aminopenicillins, such as for example ampicillin, amoxicillin and cyclacillin, are very useful antibiotics which are widely used against a large number of gram-positive and gram-negative micro-organisms.

These semisynthetic penicillins have been prepared by various processes and there is a large body of literature dealing with these methods of preparation. A number of patent applications and patents disclose preparations in which 6-aminopenicillanic acid is acylated with mixed anhydrides derived from the modified Dane salts of D-2-amino-(substituted)-acetic acid. Such methods of preparation are described in Netherlands Pat. No. 142,416; British Pat. No. 1,347,979 and U.S. Pat. Nos. 3,316,347, 3,325,479, and 4,123,611.

The Dane salts described in the literature can be either of the ester-type or the amide-type, i.e. in Dane salts having the general formula:

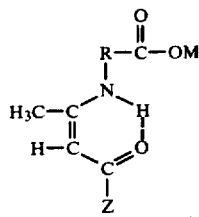

wherein

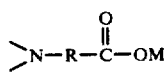

represents an amino acid moiety and M is hydrogen, an alkali metal, or a triloweralkylamine, and when Z is an alkoxy group they are of the ester-type, while when Z is an amino or substituted amino group they are of the amide-type.

The ester-type Dane salts have been widely used in preparing α-aminopenicillins and one process employing these salts is described in U.S. Pat. No. 4,128,547. In the general Dane salt/6-aminopenicillanic acid acylation process, the N-protected aminopenicillin which is formed during the acylation step is hydrolyzed to yield the desired α-aminopenicillin and, in the case of ester-type Dane salts, a β-ketoester. These β-ketoesters are generally liquids which are separated from the water-soluble α-aminopenicillin salts by extraction in an organic solvent. However, this is a significant disadvantage of the ester-type Dane salts since the β-ketoesters are not readily recovered from solution and so recycle of these β-ketoesters for the preparation of further starting Dane salts is not practicable on a commercial scale.

The amide-type Dane salts, in which Z is an amino or substituted amino group, are not as well-known as the ester-types and have not received as much attention in the literature. The amide-type Dane salts in which Z is the group $NR_1R_2$—, wherein $R_1$ is hydrogen and $R_2$ is o- or p-methoxyphenyl have been described in Chem. Ber., 98, 789 (1965) and Belgian Pat. No. 824,158. Those in which $R_1$ is hydrogen and $R_2$ is phenyl or halophenyl have been described in Swiss Pat. No. 476,758 and British Pat. No. 1,339,605. Those in which $R_1$ and $R_2$ are both alkyl or $NR_1R_2$ is morpholino have been described in Netherlands Pat. No. 142,416, British Pat. No. 1,339,605 and U.S Pat. No. 4,123,611. Those in which $R_1$ and $R_2$ are both aryl or in $NR_1R_2$ form a piperidino ring have been described in U.S. Pat. No. 4,123,611. These known amide-type Dane salts, however, have the disadvantage that they generally give poor yields of the final product α-aminopenicillins.

BRIEF DESCRIPTION OF THE INVENTION

It has been found now that the disadvantage of the prior art processes can be overcome by the use of novel amide-type Dane salts in the improved process of the present invention.

The amide-type Dane salts used in the present invention have the general formula:

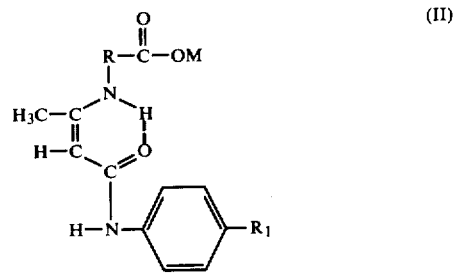

wherein R is a group of the formula:

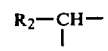

wherein $R_2$ is phenyl or substituted phenyl; $R_1$ is cyano or nitro and M is hydrogen, an alkali metal or a triloweralkylamine.

According to the improved process of the invention, α-aminopenicillins having the formula:

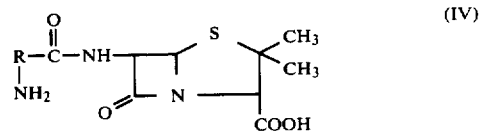

where R is defined as hereinbefore, are prepared by reacting a derivative of 6-aminopenicillanic acid in an aqueous solution, at a temperature at or below −20° C. with at least 0.8 equivalents of a mixed anhydride prepared by reacting an amide-type Dane salt (II) with an alkyl- or aralkylchloroformate in the presence of a catalyst in a mixture of acetone and dimethylacetamide or dimethylformamide, adding thereto methylene chloride, hydrolyzing the resulting N-protected aminopenicillin to yield an α-aminopenicillin and a β-ketoamide, and recovering the α-aminopenicillin and optionally, the β-ketoamide.

The term "lower alkyl" refers to groups in which the alkyl moiety has a carbon atoms content of $C_1$–$C_4$.

DETAILED DESCRIPTION OF THE INVENTION

The novel amide-type Dane salts of Formula II include those in which the grouping >N—R—COOH represents an amino acid moiety, especially that of an amino acid in which the amino group is at the α-position to the carboxyl group, which can be represented by the formula:

$$R_3-CH-COOH \quad (V)$$
$$| \atop NH_2$$

wherein $R_3$ is methylthiophenyl, phenyl, nitrophenyl, aminophenyl, hydroxyphenyl, alkoxyphenyl, or halogenophenyl. The preferred amino acids and thus amino acid moieties are those in which $R_3$ is phenyl, hydroxyphenyl or alkoxyphenyl. Most preferred are those in which $R_3$ is phenyl or p-hydroxyphenyl.

The $R_1$ substituents in Formula II include cyano and nitro, with nitro being especially preferred. It has been found that when $R_1$ is an electron-withdrawing group, such as the cyano and nitro groups, rather than an electron-donating group, such as alkyl or alkoxy, under identical conditions the yields of final product α-aminopenicillin are greatly enhanced. The nitro and cyano substituted salts are also superior to those amide-type Dane salts in which $R_1$ is hydrogen and also those in which the amide group is alkyl- or dialkylsubstituted.

The Dane salts useful in the invention include those in which M is hydrogen, an alkali metal, or a triloweralkylamine. The most preferred being the sodium salt.

The novel Dane salts are conveniently prepared by condensing an α-amino acid (VI) or a salt thereof with a β-ketoamide (VII), one method of effecting this condensation being described by Dane et al. (Angew, Chem., 1962, 74, 873).

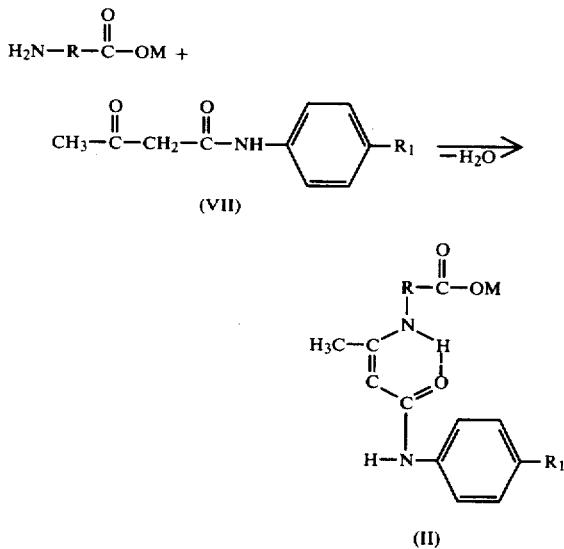

The β-ketoamides used in the above condensation are commercially available or they can be conveniently prepared according to the diketene acetoacetylation reaction described by Zavialov et al. (Tetrahedron, 1966, 22, 2003).

In accordance with the improved process of the invention, a derivative of 6-aminopenicillanic acid is reacted with a mixed anhydride formed from an amide-type Dane salt.

The mixed anhydride is prepared by reacting a Dane salt of Formula II, preferably the sodium salt, with an alkyl- or aralkylchloroformate in the presence of a catalyst in a mixture of inert, water-miscible organic solvents. The useful chloroformates include methyl chloroformate, ethyl chloroformate, isobutyl chloroformate, isopropyl chloroformate, benzyl chloroformate and the like, with ethyl chloroformate being preferred.

The preferred catalysts have the formula:

$$CH_3N{\overset{CH_2X}{\underset{CH_2Y}{\diagdown}}} \quad (VIII)$$

where X is a hydrogen atom or an alkyl, substituted alkyl, phenyl, substituted phenyl, or carboxyl group; Y is a hydrogen atom or a lower alkyl group or X and Y together represent any one of the divalent radicals ethylene, substituted ethylene, trimethylene, substituted trimethylene, —CH$_2$OCH$_2$— or —CH$_2$N(CH$_3$)CH$_2$—. Examples of such catalysts are N-methylmorpholine and N,N-dimethylbenzylamine with N-methylmorpholine being most preferred.

The inert water-miscible organic solvents used in the mixed anhydride preparation, for example, may be acetone, tetrahydrofuran, dimethylformamide or dimethylacetamide. The preferred mixtures include acetone and dimethylformamide or dimethylacetamide.

The mixed anhydride preparation is preferably carried out a temperature of −10° C. or below, most preferably at a temperature of about −20° C. to about −30° C. Since temperatures above −10° C. during the formation of the mixed anhydride favor rearrangement of the mixed anhydride to an oxazolidinone, careful regulation of this parameter is required to obtain a suitable yield of desired final product α-aminopenicillin.

The 6-aminopenicillanic acid (6-APA) is reacted with the mixed anhydride in the form of a derivative such as an alkali metal or alkaline earth salt or as a derivative of a substituted amine, the preferred amine salts being the tertiary amine salts, especially triethylamine. The appropriate 6-APA derivative is employed as an aqueous solution, to which a portion of the inert water-miscible organic solvents used in the preparation of the mixed anhydride may be added while cooling the 6-APA derivative aqueous solution to a temperature of about −20° C.

The 6-APA derivative aqueous solution need not be prepared from previously isolated 6-APA, and an aqueous solution of 6-APA obtained, for example, by the enzymatic cleavage of potassium penicillin G and the like can be used. It is a significant aspect of the process of the invention that α-aminopenicillins can be produced in high yield and purity using aqueous solutions of 6-APA obtained directly from penicillins readily produced by fermentation without first isolating the 6-APA from such aqueous solutions.

The acylation is carried out by cooling the mixed anhydride solution to a temperature of about −20° C. to about −35° C., and rapidly adding thereto the cooled aqueous solution of 6-APA derivative. It is preferable to use the mixed anhydride in an amount of at least 0.8 equivalents based on the 6-APA derivative, the useful range being 0.8–1.2 equivalents. The addition is performed with stirring at a temperature of about −20° to −35° C. Stirring is continued for a further 1-2 hours. The result of this acylation is an intermediate N-protected aminopenicillin, which is hydrolyzed in situ.

At the end of the stirring period and before the hydrolysis step, an inert, water-insoluble organic solvent, preferably methylene chloride is added to the reaction mixture.

The methylene chloride is used to extract the mixture of inert, water-miscible organic solvents from the reaction system so that following the hydrolysis step and after the reaction system separates into an organic phase and an aqueous phase, the organic solvents will have been extracted by the methylene chloride into an organic phase leaving the product α-aminopenicillin in the aqueous phase. The use of methylene chloride to extract the organic solvents from the reaction system is a significant aspect of the improved process, as it completely eliminates the use of vacuum distillation for removal of such solvents. The latter method, heretofore, has been the standard method for the removal of such typically used solvents as acetone from the reaction system after the hydrolysis step. By avoiding vacuum distillation, not only is there less product degradation, but the costs of a vacuum distillation step are eliminated.

It has also been found that if the mixed anhydride is prepared in a single solvent, such as for example, in acetone alone, the addition of methylene chloride prior to the hydrolysis step does not result in a separation of aqueous and organic layers, but requires the addition of a separation aid, such as for example sodium chloride. Such a further complication only addes another contaminant to an already complex chemical mixture. Unexpectedly, it has been discovered that if dimethylacetamide or dimethylformamide is added to the solvent used in the mixed anhydride preparation, the subsequent addition of methylene chloride prior to the hydrolysis step will result in a clean separation of the aqueous and organic phases subsequent to the hydrolysis step without the need for the addition of any separation aid. The dimethylformamide or dimethylacetamide is extracted along with the mixed anhydride solvent into the methylene chloride, and so does not interfere with subsequent recovery and purification steps.

Even more surprisingly, it has been found that if the methylene chloride is replaced by some other inert, water-insoluble organic solvent, such as methylisobutylketone, the yield of final product is decreased by up to 24%.

Accordingly, the presence of dimethylformamide or dimethylacetamide in the mixed anhydride solvent, and the addition of methylene chloride as the inert water-immiscible solvent prior to the hydrolysis step are critical aspects of the improved process.

The N-protected aminopenicillin is hydrolyzed in situ with a dilute solution of an organic acid, or an inorganic acid, such as hydrochloric acid, at a temperature of about 10° C. to about −5° C. and at a pH of about 0.9-2.0. The mixture is stirred at the same temperature for up to 45 minutes.

The aqueous and organic layers are allowed to separate, the aqueous layer, containing the desired final product, is washed with an inert, water-insoluble organic solvent, such as ethyl acetate, methylisobutyl ketone or methylene chloride. The organic layer, containing the β-ketoamide liberated from the N-protected aminopenicillin during hydrolysis, is washed with water and the wash water is added to the aqueous layer. The aqueous layer is filtered, adjusted to the isoelectric point of the α-aminopenicillin, allowed to crystallize and the desired final product α-aminopenicillin recovered.

The organic layer and the organic solvent washes of the aqueous layer are combined, filtered and concentrated to dryness. The residual oil is diluted with an organic solvent, filtered, diluted with water, and allowed to stir at room temperature for 2 hours. The liberated β-ketoamide crystallizes and is recovered. The latter, which is recovered at a high degree of purity and in high yields, is readily recycled for the preparation of further starting amide-type Dane salts.

The improved process of the invention, using novel amide-type Dane salts, advantageously gives high yields of α-aminopenicillins at the required high degree of purity with minimal losses of 6-APA and product α-aminopenicillin. The high concentrations of starting, intermediate, and final materials allows for a high throughput. Moreover, the absence of the hitherto usual organic solvent vacuum distillation step subsequent to acylation results in less product degradation and the elimination of the costs involved in vacuum distillation. The recyclable nature of the β-ketoamide liberated during hydrolysis provides a very significant advantage to process economics, as the readily recovered crystalline β-ketoamides are re-used in further preparation of the amide-type Dane salts.

The following examples illustrate preferred embodiments of the invention, but the invention is not intended to be limited thereby.

EXAMPLE 1

D-2-(4-Hydroxyphenyl)-N-[1-methyl-2-(4-nitrophenylcarbamoyl)vinyl]glycine, sodium salt A 5 L. 4-neck flask, fitted with a stirrer, thermometer, reflux condenser, nitrogen inlet and drying tube, is charged with 2.6 L. of methanol and 117 g. (2.88 moles) of sodium hydroxide pellets. The mixture is heated to reflux and stirred until all sodium hydroxide is dissolved. Then 457 g. (2.74 moles) of D(−)-p-hydroxyphenylglycine is added, followed by 640 g. (2.88 moles) of p-nitroacetoacetanilide. The reaction mixture is reheated and kept at reflux for 30 minutes. After removal of the heat source, the stirring is continued for 60 minutes and then the mixture is stirred for 3 hours at 3° C. The precipitate is collected by filtration and washed with 0.5 L. of methanol. The product is dried in an air oven at 4° C. overnight to obtain 927 g. (86.1% yield) of the title compound. Upon concentration of mother liquor and wash, a further 129 g. (12%) of product is isolated. Melting point: 260°-265° C. dec.

EXAMPLE 2

D-2-(4-Hydroxyphenyl)-N-[1-methyl-2-(4-nitrophenylcarbamoyl)vinyl]glycine, potassium salt The title compound is prepared in 89.3% yield by a procedure similar to Example 1. Melting point: 220°-245° C. dec.

EXAMPLE 3

D-N-[2-(4-Cyanophenylcarbamoyl)-1-methylvinyl]-2-(4-hydroxyphenyl)glycine, potassium salt The title compound is prepared in a similar manner as Example 1 in 78.8% yield using p-cyanoacetoacetanilide. When methanol is replaced by ethanol, the title compound is obtained in 92.3% yield. Melting point: 250°–255° C. dec.

EXAMPLE 4

D-N-[2-(4-Cyanophenylcarbamoyl)-1-methylvinyl]-2-(4-hydroxyphenyl)glycine, sodium salt The title compound is prepared in a similar manner as Example 1, using sodium hydroxide and methanol in 55.3% yield. Melting point: 230°–240° C. dec.

EXAMPLE 5

D-N-[1-Methyl-2-(4-nitrophenylcarbamoyl)vinyl]-2-phenylglycine, sodium salt

The title compound is prepared in a similar manner as Example 1 using D(−)phenylglycine, methanol and sodium hydroxide in 81.4% yield. Melting point: 220°–230° C. dec.

EXAMPLE 6

D-N-[1-Methyl-2-(4-nitrophenylcarbamoyl)vinyl]-2-phenylglycine, potassium salt

The title compound is prepared in a similar manner as Example 1, using D(−)-phenylglycine, methanol, and potassium hydroxide, in 86% yield. Melting point: 170°–178° C.

EXAMPLE 7

D-N-[2-(4-cyanophenylcarbamoyl)-1-methylvinyl]-2-phenylglycine potassium salt

The title compound is prepared in a similar manner as Example 1 using D(−)-phenylglycine, ethanol and potassium hydroxide in 89.3% yield. Melting point: 225°–235° C. dec.

EXAMPLE 8

6-[D(−)-α-amino-p-hydroxyphenylacetamido]penicillanic acid, trihydrate

A. Preparation of Mixed Anhydride

A 5 L. 4-neck flask, fitted with a stirrer, thermometer, nitrogen inlet and drying tube, is charged with 800 ml. acetone, 200 ml. dimethylformamide, 6 ml. water, and 1 ml. N-methylmorpholine. The mixture is cooled under nitrogen to −20°±2° C., and 113 g. (0.288 mole) D-2-(4-hydroxyphenyl)-N-[1-methyl-2-(4-nitrophenylcarbamoyl)vinyl]glycine sodium salt, prepared according to Example 1, is added all at once followed by 28.7 ml. (0.293 mole) of ethylchloroformate. The mixture is allowed to stir for one hour at −20°±2° C.

B. Preparation of 6-APA Derivative

To a 2 L. 4-neck flask fitted with stirrer, thermometer, and pH-electrode is charged 54 g. (0.25 mole) of 6-aminopenicillanic acid and 200 ml. of water. The mixture is cooled to 3° C. and the pH is adjusted to 8.0±0.2 by the gradual addition of approximately 100 ml. of 2.5 N. aqueous potassium hydroxide solution to dissolve the 6-aminopenicillanic acid completely. The mixture is cooled to −20° C.±2° C. while adding 300 ml. of acetone.

C. Preparation of 6-[D(−)-α-Amino-p-hydroxyphenylacetamido]penicillanic acid, trihydrate The 6-aminopenicillanic acid potassium salt solution of B above is added to the mixed anhydride mixture of A above all at once and the mixture is stirred for one hour at −20°±2° C. and then is allowed to warm up to −10° C. over a period of 30 minutes. 600 ml. of methylene chloride and a mixture of 45 ml. of concentrated hydrochloric acid and 500 ml. of water are added and the entire mixture is stirred for 15 minutes at 3°–5° C. The aqueous and organic layers are allowed to separate and the organic layer is washed once with 100 ml. of water. The combined aqueous phase and wash are washed twice with 250 ml. of methylene chloride. The aqueous phase is filtered through a Celite-covered filter and adjusted to pH 5.2 by gradual addition of approximately 35 ml. of concentrated ammonium hydroxide at 5°±2° C. The mixture is stirred for two hours at 3°–5° C.

The product is collected by filtration and washed with water and acetone. The product is slurried in 400 ml. of 80% aqueous acetone, filtered and washed with 100 ml. of 80% aqueous acetone. The product is dried to constant weight at 40° C. to obtain 74.6 g. (71%) of title compound, iodometric assay 850 mcg/mg.

D. Recovery of p-Nitroacetoacetanilide

The organic layer and washes are combined and concentrated to approximately 360 ml. of an oil, which is diluted with 150 ml. of isopropanol and filtered. The solution is diluted with 750 ml. of water and vigorously stirred for 2 hours at room temperature. The product is collected by filtration, washed with 500 ml. of water, slurried in 100 ml. of isopropanol and filtered again. 47 g. (74%) p-nitroacetoacetanilide, m.p. 116°–118° C., is recovered. This material is used to prepare D-2-(4-hydroxyphenyl)-N-[1-methyl-2-(4-nitrophenylcarbamoyl)vinyl]glycine, sodium salt, in the same way and with the same yield as in Example 1.

EXAMPLE 8A

Variations in the Procedure of Example 8

The preparation procedures of Example 8 are carried out, but the mixed anhydride solvent system is changed and the methylene chloride is replaced with methylisobutylketone. The effects on yield of final product are noted.

A. The dimethylformamide of Example 8, step A is omitted and the quantity of omitted dimethylformamide is compensated for by a comparable increase in the quantity of acetone used, i.e. 1000 ml. of acetone vs. 800 ml. acetone + 200 ml. dimethylformamide. After following the remainder of the procedures, there is obtained 57.1% yield of amoxicillin trihydrate. This is a significant drop in yield from the 71% obtained in Example 8.

B. The methylene chloride of Example 8, step C is replaced with a like quantity of methylisobutylketone. After following the remainder of the procedures, there is obtained a 46.7% yield of amoxicillin tryhydrate. This is a very significant decrease in yield from the 71% obtained in Example 8.

EXAMPLE 9

6-[D(−)-α-Amino-p-hydroxyphenylacetamido]penicillanic acid, trihydrate

Following the procedure of Example 8 and using 1200 ml. acetone, 240 ml. dimethylacetamide, 10 ml. water, 2 ml. N-methylmorpholine, 99 g. (0.25 mole) D-2-(4-hydroxyphenyl)-N-[1-methyl-2-(4-nitrophenylcarbamoyl)vinyl]glycine sodium salt prepared according to Example 1, 25 ml. (0.26 mole) ethylchloroformate, and 1000 ml. of methylene chloride there is obtained 69 g. (65.8%) of title compound, iodometric assay 868 mcg/mg. Recovery of p-nitroacetoacetanilide is 49 g. (88.3%), m.p. 119°-122° C.

EXAMPLE 10

6-[D(−)-α-Amino-p-hydroxyphenylacetamido]penicillanic acid, trihydrate

Following the procedure of Example 8 and using 127 g. (0.326 mole) of D-(−)N-[2-(4-cyanophenylcarbamoyl)-1-methylvinyl]-2-(4-hydroxyphenyl)glycine potassium salt prepared according to Example 3 and 32.6 ml. (0.34 mole) of ethylchloroformate and extending the hydrolysis from 15 to 45 mins., there is obtained 71.6 g. (68.2%) of title compound, iodometric assay 835 mcg/mg. Recovery of p-cyanoacetoacetanilide is 44.5 g. (67.6%), m.p. 122°-125° C.

EXAMPLE 11

6-[D(−)-α-aminophenylacetamido]penicillanic acid, anhydrous

6-[D(−)-α-aminophenylacetamido]penicillanic acid (ampicillin) naphthalene sulfonic acid salt is prepared by a procedure similar to that in Example 8, except that 111 g. (0.288 mole) of D-(−)-N-[1-methyl-2-(4-nitrophenylcarbamoyl)vinyl]-2-phenyl glycine sodium salt prepared according to Example 5 is used. To the final aqueous ampicillin solution is added 100 ml. of ethyl acetate and 200 g. of aqueous β-naphthalene sulfonic acid solution (29% weight/volume) while the pH is adjusted to 1.2 at 5°-10° C. by the concurrent addition of triethylamine. The resulting thick slurry is stirred overnight at 0°-5° C. The product is filtered on a Buchner funnel and washed with water and ethyl acetate.

The wet filter cake is treated with one equivalent of triethylamine in 85% aqueous isopropanol at 65° C. for 30 minutes, filtered and dried to give 59.5 g. of anhydrous ampicillin for a yield of 80.6%, iodometric assay, 986 mcg/mg. Recovery of p-nitroacetoacetanilide is 47 g. (73.6%), m.p. 117°-119° C.

EXAMPLE 12

6-[D(−)-α-aminophenylacetamido]penicillanic acid, anhydrous

Following the procedure of Example 11 and using 600 ml. acetone, 160 ml. dimethylformamide, 5 ml. water, 95 g. (0.25 mole) D-(−)-N-[1-methyl-2-(4-nitrophenylcarbamoyl)vinyl]-2-phenylglycine sodium salt prepared according to Example 5, and 25 ml. (0.26 mole) ethylchloroformate, there is obtained 116.9 g. (83.9%) of ampicillin β-naphthalenesulfonate, which is converted to 59.7 g. (81.5%) of anhydrous ampicillin, iodometric assay 982 mcg/mg. Recovery of p-nitroacetoacetanilide is 45 g. (81%), m.p. 117°-119° C.

EXAMPLE 13

6-[D(−)-α-aminophenylacetamido]penicillanic acid, anhydrous

Following the procedure of Example 11 and using 107 g. (0.288 mole) D-(−)-N-[2-(4-cyanophenylcarbamoyl)-1-methylvinyl]-2-phenylglycine potassium salt prepared according to Example 7, there is obtained 129.5 g. (92.9%) of ampicillin β-naphthalenesulfonate, which is converted to 63.5 g. (78.2%) of anhydrous ampicillin, iodometric assay 990 mcg/mg. Recovery of p-cyanoacetoacetanilide is 48.8 g. (84%), m.p. 123°-125° C.

EXAMPLE 14

The preparative procedures of Example 11 are carried out, but the mixed anhydride solvent system is changed. The effects of the changes on yield of final product are noted.

A. The dimethylformamide in the mixed anhydride solvent system of Example 11 is replaced with a comparable quantity of N-methylpyrrolidinone or hexamethylphosphoramide. After following the remainder of the procedures, there are obtained the following yields of products:

|  | Yield of Ampicillin Naphthalenesulfonic Acid | Yield of Anhydrous Ampicillin |
| --- | --- | --- |
| N—Methylpyrrolidinone | 77.1% | 63.8% |
| Hexamethylphosphoramide | 68.4% | 61.0% |

This is in marked constrast to the yields of 83.9% and 81.5%, respectively, obtained in Example 12 and the yields of 92.9% and 78.2%, respectively, obtained in Example 13, and the yield of 80.6% of anhydrous ampicillin obtained in Example 11.

What is claimed is:

1. A process for preparing an α-aminopenicillin having the formula:

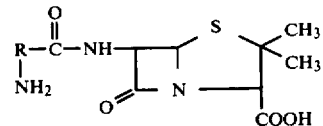

wherein R is a group having the formula:

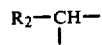

wherein $R_2$ is phenyl or substituted phenyl, and physiologically acceptable salts thereof, which comprises reacting a derivative of 6-aminopenicillanic acid in an aqueous solution at a temperature at or below −20° C. with at least 0.8 equivalent of a mixed anhydride prepared by reacting an amide-type Dane salt having the formula:

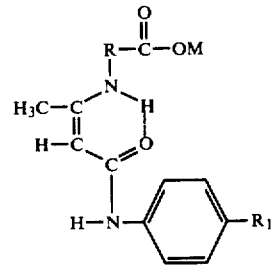

wherein R is a defined hereinbefore and $R_1$ is cyano or nitro and M is an alkali metal or triloweralkylamine, with an alkyl- or aralkylchlorocarbonate in the presence of a catalyst in a mixture of acetone and dimethylformamide or dimethylacetamide, adding thereto methylene chloride, hydrolyzing the resulting N-protected aminopenicillin to yield an α-aminopenicillin and a β-ketoamide, and recovering the α-aminopenicillin and the β-ketoamide.

2. The process of claim 1, wherein said recovered β-ketoamide is recycled for preparation of the amide-type Dane salt.

3. The process of claim 1, wherein said mixed anhydride is prepared at a temperature of −10° C. or below.

4. The process of claim 1, wherein said catalyst is N-methylmorpholine.

5. The process of claim 1, wherein said 6-aminopenicillanic acid derivative is an alkali metal, an alkaline earth metal or a trialkylamine salt of 6-aminopenicillanic acid.

6. The process of claim 1, wherein the product α-aminopenicillin is 6-[D(−)-α-amino-p-hydroxyphenylacetamido]penicillanic acid.

7. The process of claim 1, wherein the product α-aminopenicillin is 6-[D(−)-α-aminophenylacetamido]penicillanic acid.

* * * * *